(12) United States Patent
Jeong et al.

(10) Patent No.: US 8,362,471 B2
(45) Date of Patent: Jan. 29, 2013

(54) AROMATIC ENEDIYNE DERIVATIVE, ORGANIC SEMICONDUCTOR THIN FILM, ELECTRONIC DEVICE AND METHODS OF MANUFACTURING THE SAME

(75) Inventors: Eun Jeong Jeong, Yongin-si (KR); Hyun Sik Moon, Yongin-si (KR); Jeong Ii Park, Yongin-si (KR); Sang Yoon Lee, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 2 days.

(21) Appl. No.: 12/929,078

(22) Filed: Dec. 29, 2010

(65) Prior Publication Data

US 2011/0098486 A1    Apr. 28, 2011

Related U.S. Application Data (62) Division of application No. 11/806,742, filed on Jun. 4, 2007, now Pat. No. 7,884,358.

(30) Foreign Application Priority Data

Nov. 17, 2006 (KR) .................. 10-2006-0113845

(51) Int. Cl.
*H01L 35/24* (2006.01)
(52) U.S. Cl. ............................ 257/40; 549/59; 556/431
(58) Field of Classification Search .................. None
See application file for complete search history.

(56) References Cited

U.S. PATENT DOCUMENTS 6,683,782 B2    1/2004  Duva
8,026,663 B2 *  9/2011  Matsumoto et al. .......... 313/504

FOREIGN PATENT DOCUMENTS

WO    WO2006/038709    *  4/2006

OTHER PUBLICATIONS

Jiang et al JOC, 2005, 71, 2155-2158.*
Palmer, et al., (Synthesis of a remarkably stable dehydro[14]annulene, Angewandte Chemie, International Edition (2001), 40(13), 2509-2512.

* cited by examiner

*Primary Examiner* — Yevegeny Valenrod
(74) *Attorney, Agent, or Firm* — Harness, Dickey & Pierce, P.L.C.

(57) ABSTRACT

Disclosed are a novel aromatic enediyne derivative, an organic semiconductor thin film using the same, and an electronic device. Example embodiments pertain to an aromatic enediyne derivative which enables the formation of a chemically and electrically stable and reliable semiconductor thin film using a solution process, e.g., spin coating and/or spin casting, at about room temperature when applied to devices, an organic semiconductor thin film using the same, and an electronic device including the organic semiconductor thin film. A thin film having a relatively large area may be formed through a solution process, therefore simplifying the manufacturing process and decreasing the manufacturing cost. Moreover, it is possible to provide an organic semiconductor that may be effectively applied to various fields including organic thin film transistors, electroluminescent devices, solar cells, and memory.

14 Claims, 2 Drawing Sheets

AROMATIC ENEDIYNE DERIVATIVE, ORGANIC SEMICONDUCTOR THIN FILM, ELECTRONIC DEVICE AND METHODS OF MANUFACTURING THE SAME

PRIORITY STATEMENT

This application is a Divisional of U.S. application Ser. No. 11/806,742 filed Jun. 4, 2007, now U.S. Pat. No. 7,884,358 which claims priority from Korean Patent Application No. 2006-0113845, filed on Nov. 17, 2006, in the Korean Intellectual Property Office, the entire contents of each of which are herein incorporated by reference.

BACKGROUND

1. Field

Example embodiments relate to an aromatic enediyne derivative, an organic semiconductor thin film, an electronic device and methods of manufacturing the same. Other example embodiments relate to an aromatic enediyne derivative, an organic semiconductor thin film, which may be prepared from the aromatic enediyne derivative through a solution process, e.g., spin coating and/or spin casting, at about room temperature, and has improved chemical and electrical stability and reliability, an electronic device comprising the organic semiconductor thin film and methods of manufacturing the same.

2. Description of the Related Art

In general, flat display devices, e.g., liquid crystal displays and/or organic electroluminescent displays, are provided with a variety of thin film transistors (TFTs) to drive them. The TFT may include a gate electrode, source/drain electrodes, and a semiconductor layer that is activated depending on the operation of the gate electrode. The p-type or n-type semiconductor layer may function as a conductive channel material for controlling the current between the source electrode and the drain electrode using the applied gate voltage.

As the semiconductor for TFTs, amorphous Si (a-Si) and polycrystalline Si (poly-Si) are mainly used. With the recent trend toward increased area, decreased price, and flexibility of displays, research has been directed toward semiconductors using organic material, in place of expensive inorganic material requiring a high-temperature vacuum process.

Using low-molecular-weight organic material, e.g., pentacene, as the organic semiconductor material has been studied. In this regard, the low-molecular-weight organic material, e.g., pentacene, has been reported to have increased charge mobility of about 3.2 $cm^2/Vs$~about 5.0 $cm^2/Vs$ or more and an improved on/off current ratio, but suffers because the low-molecular-weight organic material may require an expensive apparatus for vacuum deposition upon formation of a thin film and may be difficult to use to form a fine pattern, and therefore may be unsuitable for inexpensive preparation of a film having a relatively large area.

Further, as an oligomer-based organic semiconductor, a soluble pentacene precursor capable of being annealed at about 120° C.~about 200° C. and having a charge mobility of about 0.1 $cm^2/VS$ has been reported. In addition, an oligothiophene precursor, which has charge mobility of about 0.03 $cm^2/Vs$~about 0.05 $cm^2/Vs$ and may be annealed at about 180° C.~about 200° C., has been reported. However, such organic semiconductors may be chemically unstable during processing for fabrication of a device and are thus difficult to implement in an actual device fabrication line. With regard to electrical stability, when the current-electron sweeping is repeated, decreased voltage and decreased reliability may be undesirably incurred.

Examples of the related art disclose an organic compound having an acetylene group and a method of preparing a thin film through a vacuum deposition process using such a compound. However, this method may require a vacuum deposition process in order to prepare a thin film, and may be unsuitable for the inexpensive preparation of a film having a relatively large area, as with pentacene.

SUMMARY

Accordingly, example embodiments have been made keeping in mind the above problems occurring in the related art, and example embodiments provide an aromatic enediyne derivative, which enables the preparation of a chemically and electrically stable and reliable organic semiconductor through a solution process, e.g., spin coating and/or spin casting, at about room temperature when applied to devices.

Example embodiments provide an organic semiconductor thin film comprising the aromatic enediyne derivative, an electronic device comprising the organic semiconductor thin film, a method of manufacturing an organic semiconductor thin film using the aromatic enediyne derivative and a method of manufacturing an electronic device. The organic semiconductor thin film functions as a carrier transport layer in the electronic device.

Example embodiments provide an aromatic enediyne derivative represented by any one of Formulas 1 to 3 below:

Formula 1

Formula 2

Formula 3 in Formulas 1 to 3, $R_1$, $R_2$, $R_3$, and $R_4$ are each independently selected from the group consisting of hydrogen, halogen, a nitro group, an amino group, a cyano group, —$SiR^1R^2R^3$ (in which $R^1$, $R^2$, and $R^3$ are each independently hydrogen or a $C_1$-$C_{10}$ alkyl group), a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted $C_6$-$C_{20}$ arylalkyl group, a substituted or unsubstituted $C_6$-$C_{30}$ aryloxy group, a substituted or unsubstituted $C_2$-$C_{30}$ heteroaryloxy group, a substituted or unsubstituted $C_1$-$C_{20}$ heteroalkyl group, and a substituted or unsubstituted $C_2$-$C_{30}$ heteroarylalkyl group, provided that none of $R_1$, $R_2$, $R_3$, and $R_4$ are hydrogen, X is carbon or a heteroatom, including nitrogen, oxygen, sulfur or selenium (Se), and Ar is selected from the group consisting of a substituted or unsubstituted $C_2$-$C_{30}$ fused arylene group and a substituted or unsubstituted $C_2$-$C_{30}$ fused heteroarylene group, and is condensed with acetylene-substituted rings on both sides thereof.

BRIEF DESCRIPTION OF THE DRAWINGS

Example embodiments will be more clearly understood from the following detailed description taken in conjunction with the accompanying drawings. FIGS. 1-3 represent non-limiting, example embodiments as described herein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. In particular, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF EXAMPLE EMBODIMENTS

Hereinafter, a detailed description will be given of example embodiments with reference to the appended drawings. In the drawings, the thicknesses and widths of layers are exaggerated for clarity. Example embodiments may, however, be embodied in many different forms and should not be construed as limited to the example embodiments set forth herein. Rather, these example embodiments are provided so that this disclosure will be thorough and complete, and will fully convey the scope of example embodiments to those skilled in the art.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numbers refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to example embodiments, the aromatic enediyne derivative may be represented by any one of Formulas 1 to 3 below:

Formula 1

Formula 2

Formula 3 in Formulas 1 to 3, $R_1$, $R_2$, $R_3$, and $R_4$ are each independently selected from the group consisting of hydrogen, halogen, a nitro group, an amino group, a cyano group, $-SiR^1R^2R^3$ (in which $R^1$, $R^2$, and $R^3$ are each independently hydrogen or a $C_1$-$C_{10}$ alkyl group), a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted $C_6$-$C_{20}$ arylalkyl group, a substituted or unsubstituted $C_6$-$C_{30}$ aryloxy group, a substituted or unsubstituted $C_2$-$C_{30}$ heteroaryloxy group, a substituted or unsubstituted $C_1$-$C_{20}$ heteroalkyl group, and a substituted or unsubstituted $C_2$-$C_{30}$ heteroarylalkyl group, provided that none of $R_1$, $R_2$, $R_3$, and $R_4$ are hydrogen, X is carbon or a heteroatom, including nitrogen, oxygen, sulfur or selenium (Se), and Ar is selected from the group consisting of a substituted or unsubstituted $C_2$-$C_{30}$ fused arylene group and a substituted or unsubstituted $C_2$-$C_{30}$ fused heteroarylene group, and is condensed with acetylene-substituted rings on both sides thereof.

Further, the substituent of $R_1$, $R_2$, $R_3$, and $R_4$ may be a halogen atom, a hydroxyl group, a nitro group, a cyano group, an amino group, an amide group, or a carboxyl group, and at least one hydrogen atom of Ar in the above formulas may be substituted with halogen, a nitro group, an amino group, a cyano group, $-SiR^1R^2R^3$ (where $R^1$, $R^2$, and $R^3$ are each independently hydrogen or a $C_1$-$C_{10}$ alkyl group), a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted $C_6$-$C_{20}$ arylalkyl group, a substituted or unsubstituted $C_6$-$C_{30}$ aryloxy group, a substituted or unsubstituted $C_2$-$C_{30}$ heteroaryloxy group, a substituted or unsubstituted $C_1$-$C_{20}$ heteroalkyl group, and a substituted or unsubstituted $C_2$-$C_{30}$ heteroarylalkyl group.

A conventional plastic substrate used in the fabrication of flexible displays cannot endure a heat-curing temperature of about 150° C. or higher, thus causing problems related to light weight and flexibility. However, in example embodiments, as low-molecular-weight semiconductor material having conjugated chains, the aromatic enediyne derivative may be used to manufacture an organic semiconductor thin film, thereby enabling the use of a solution process at decreased temperatures, leading to an organic semiconductor thin film having both the regular molecular arrangement of the low-molecular-weight semiconductor and the electrical stability of the polymer. The aromatic enediyne derivative of example embodiments may be structured in such a way that one acetylene group is respectively attached to each end of a double bond of an aromatic substituent thereof in order to form an unsaturated core. Accordingly, the aromatic enediyne derivative may have a specific chemical structure and active mechanism for realizing increased reactivity, and therefore a radical benzene ring may be easily formed even at decreased temperatures, thereby achieving polymerization through intramolecular or intermolecular bonding.

Although Ar of the aromatic enediyne derivative of Formulas 1 to 3 is not particularly limited, it may be selected from the group represented by Formula 4 below, for example, a thiophene group or a phenyl group may be useful in order to increase the mobility of a semiconductor. In the aromatic enediyne derivative of Formulas 1 to 3, Ar may be condensed with acetylene-substituted rings on both sides thereof.

Formula 4 wherein Y is carbon or a heteroatom, including nitrogen, oxygen, sulfur or selenium (Se), and n is about 0 or a positive integer from about 1 to about 4.

The aromatic enediyne derivative of example embodiments may be synthesized using a conventional process without particular limitation. Such an aromatic enediyne derivative may be used as a material for an organic semiconductor constituting an active layer and thus may be effectively applied to the fabrication of various electronic devices, e.g., TFTs, electroluminescent (EL) devices, solar cells, and/or memory.

In addition, example embodiments provide an organic semiconductor thin film, manufactured using the aromatic enediyne derivative, and a manufacturing method thereof.

The organic semiconductor thin film of example embodiments may be manufactured by i) applying a precursor solution, including the aromatic enediyne derivative represented by any one of Formulas 1 to 3 and an organic solvent, on a substrate to form a coating film and ii) heating the coating film for crosslinking thereof.

As such, the precursor solution may be prepared by mixing two or more aromatic enediyne derivatives represented by Formulas 1 to 3. Further, such an aromatic enediyne derivative may be contained in the precursor solution in an amount of about 0.001 wt %~about 30 wt %.

The organic solvent used in example embodiments may not be particularly limited, examples thereof including an aliphatic hydrocarbon solvent, e.g., hexane and/or heptane, an aromatic hydrocarbon solvent, e.g., toluene, pyridine, quinoline, anisol, mesitylene, xylene and/or chlorobenzene, a ketone-based solvent, e.g., methyl isobutyl ketone, 1-methyl-2-pyrrolidinone, cyclohexanone or acetone, an ether-based solvent, e.g., tetrahydrofuran and/or isopropyl ether, an acetate-based solvent, e.g., ethyl acetate, butyl acetate and/or propyleneglycol methyl ether acetate, an alcohol-based solvent, e.g., isopropyl alcohol and/or butyl alcohol, an amide-based solvent, e.g., dimethylacetamide and/or dimethylformamide, a halogen-based solvent, e.g., dichloromethane and/or trichloromethane, a silicon-based solvent, and mixtures thereof.

In this way, when the precursor solution composed of the aromatic enediyne derivative and the organic solvent is prepared, the precursor solution may be applied on a substrate, thus forming a coating film.

In example embodiments, the substrate for use in the formation of the organic semiconductor thin film may not be particularly limited as long as it does not inhibit the purpose of example embodiments, examples thereof including a glass substrate, a silicon wafer, ITO glass, quartz, a silica substrate, an alumina substrate and/or a plastic substrate.

Examples of the process of applying the precursor solution on the substrate may include spin coating, dip coating, roll coating, screen coating, spray coating, spin casting, flow coating, screen printing, ink jetting, and drop casting. Among them, spin coating is particularly useful in the interest of convenience and uniformity. Where spin coating is performed, the spin rate may be set in the range from about 100 rpm to about 10,000 rpm.

Subsequently, the resultant coating film may be heated to allow it to crosslink, thereby obtaining a desired thin film. Such heat treatment may be conducted at about 100° C.~about 250° C., and may be carried out for about 1 min~about 100 min at an appropriate temperature within the above temperature range, or alternatively, may be carried out while gradually increasing the temperature.

The crosslinking mechanism of the aromatic enediyne derivative may be represented by Reaction 1 below:

Reaction 1

-continued

As is apparent from Reaction 1, the acetylene groups attached to the double bonds of the aromatic enediyne derivative may be formed into radical benzene rings at a predetermined or given reaction temperature due to the increased reactivity of the active mechanism of enediyne, resulting in a polymer network through intramolecular or intermolecular bonding.

Where a semiconductor thin film is formed using a conventional precursor solution, the thin film may crack due to the emission of gas created by the intermolecular bonding or solvent during the heat treatment. However, the organic semiconductor thin film of example embodiments may be polymerized through the radical reaction using the increased reactivity of the active mechanism of enediyne, thereby preventing or retarding the thin film from cracking, which may occur due to the generation of gas during a continuous process. The crosslinking reaction may progress without the use of an additive, thus preventing or reducing the negative effect of interrupting the molecular arrangement due to the use of the additive, which acts as an impurity.

In addition, example embodiments provide an electronic device, comprising the organic semiconductor thin film as a carrier transport layer.

The organic semiconductor thin film thus formed may maintain improved transistor properties due to intermolecular packing based on the regular arrangement of a monomolecular aromatic enediyne derivative and intermolecular cross-network formation, and may also assure chemical and electrical stability and reliability upon formation into a polymeric thin film. Where the organic semiconductor thin film is applied as the carrier transport layer to electronic devices, improved properties may be provided and the cost reduction effect may be maximized or increased by realizing a solution process at about room temperature.

Specific examples of the electronic device may include OTFTs, EL devices, solar cells and/or memory. The aromatic enediyne derivative of example embodiments may be applied to the above devices using a conventional process known in the art.

A better understanding of example embodiments may be obtained in light of the following examples which are set forth to illustrate, but are not to be construed to limit example embodiments.

PREPARATIVE EXAMPLE 1

Synthesis of Aromatic Enediyne Derivative

-continued

-continued

About 1 equivalent of dialdehyde and about 0.5 equivalents of 1,6-cyclohexadione were dissolved in ethanol, and about 5% aqueous NaOH was slowly added thereto. After being allowed to stand overnight, the precipitate was filtered and dried. About 3 equivalents of trimethylsilyl acetylene, about 0.1 equivalents of $PdCl_2(PPh_3)_2$ and about 0.05 equivalents of CuI were refluxed in THF and diisopropylamine for about 10 hours, thus obtaining a tetraethynyl compound.

The tetraethynyl compound in THF was slowly added with a Grignard reagent made using about 3 equivalents of trimethylsilyl acetylene, and then refluxed for about 3 hours. Aqueous $SnCl_2$ was added to the reactor, and then stirred at about room temperature for about 1 hour. The resultant organic layer was washed with water and chloroform, dried, and then purified through silica column chromatography, thus yielding product 1. 1H NMR (300 MHz, $CDCl_3$) d (ppm) 0.37 (s, 18H), 0.90-0.95 (m, 18H), 1.12-1.27 (m, 22H), 1.31-1.38 (m, 8H), 1.67-1.72 (m, 4H), 2.60 (t, 4H, J=6.8 Hz), 3.59 (s, 2H), 8.95 (s, 2H), 9.09 (s, 2H)

The product 1 was dissolved in $CHCl_3$, added with methanol and THF, further added with an excess of about 1N aqueous NaOH, and then allowed to react. The resultant reaction product was washed with water, and the organic layer was dried and then purified via silica column chromatography, thus yielding a compound 2. 1H NMR (300 MHz, $CDCl_3$) d (ppm) 0.88-0.96 (m, 18H), 1.12-1.30 (m, 22H), 1.31-1.40 (m, 8H), 1.67-1.72 (m, 4H), 2.61 (t, 4H, J=6.9 Hz), 3.59 (s, 2H), 8.95 (s, 2H), 9.17 (s, 2H)

EXAMPLE 1

Preparation of Organic Semiconductor Thin Film

On a washed plastic substrate, aluminum/niobium (Al/Nb) alloy for a gate electrode was deposited to about 1000 Å through sputtering, and then $SiO_2$ for a gate insulating film was deposited to about 1000 Å using CVD.

Figure 3:
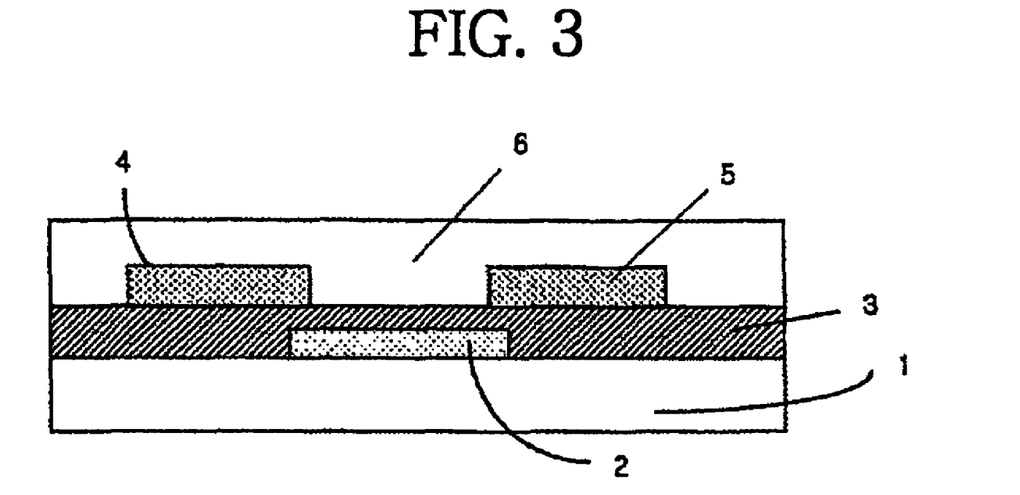
FIG. 3 is a schematic sectional view showing the organic thin film transistor (OTFT) of example embodiments.

Subsequently, Au for source/drain electrodes was deposited to about 1200 Å thereon through sputtering. Before being coated with the organic semiconductor material, the substrate was washed using isopropyl alcohol for about 10 min and then dried. The sample was dipped into a about 10 mM octadecyltrichlorosilane solution in hexane for about 30 sec, washed with acetone, and then dried. Thereafter, the aromatic enediyne derivative of Preparative Example 1 was dissolved to about 0.1 wt % in a xylene solvent, applied on the substrate via dropping, and then baked at about 100° C. for about 30 min in an argon atmosphere, thereby fabricating the bottom-contact-type OTFT as seen in FIG. 3.

EXAMPLE 2

Fabrication of OTFT

An OTFT was fabricated in the same manner as in Example 1, with the exception that, in the annealing process, the baking was conducted at about 160° C. for about 30 min.

The DSC of the aromatic enediyne derivative synthesized in Preparative Example 1 was measured. The results are shown in FIG. 1.

Figure 1:
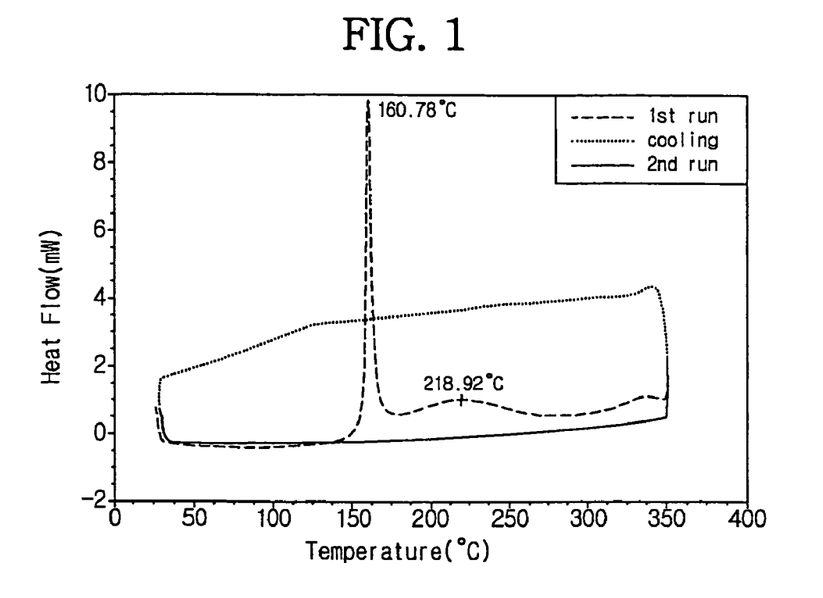
FIG. 1 is a graph showing the result of differential scanning calorimetry (DSC) of the aromatic enediyne derivative synthesized in Preparative Example 1 of example embodiments.

As shown in FIG. 1, the aromatic enediyne derivative of example embodiments was found to begin to crosslink at about 150° C. and then to actively react at about 170° C. or lower. As is apparent from these results, the aromatic enediyne derivative of example embodiments may be formed into a semiconductor thin film through a low-temperature wet process.

Further, the TGA of the aromatic enediyne derivative of Preparative Example 1 was measured. The results are shown in FIG. 2.

Figure 2:
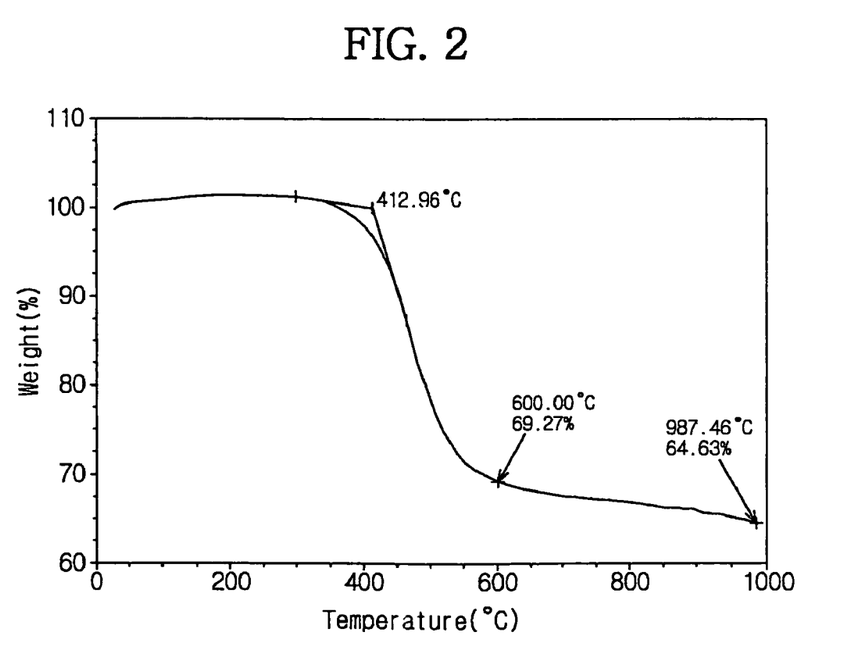
FIG. 2 is a graph showing the result of thermogravimetry analysis (TGA) of the aromatic enediyne derivative synthesized in Preparative Example 1 of example embodiments.

As seen in FIG. 2, the aromatic enediyne derivative of example embodiments did not lose any weight up to about 300° C. The aromatic enediyne derivative of example embodiments did not lose weight even at a temperature exceeding the reaction temperature of about 150° C.~about 170° C., which indicates that no more gas was generated from the resultant polymer. Therefore, where the semiconductor thin film was formed using the aromatic enediyne derivative of example embodiments, the problem of cracking of the thin film attributable to the generation of gas may be prevented or reduced. In addition, this is judged to be because triple bonds ($C{\equiv}C$) and hydrogen bond ($\equiv$C—H) attached thereto induced intramolecular or intermolecular bonding in proportion to the increase in the annealing temperature, such that the benzene ring was formed and polymerization was realized according to the active mechanism of enediyne when the temperature was increased.

In order to evaluate the electrical properties of the OTFTs fabricated in Examples 1 and 2, the current transfer properties thereof were measured using a semiconductor characterization system (4200-SCS), available from KEITHLEY, and then charge mobility and cut-off leakage current were calculated. The results are given in Table 1 below.

The charge mobility was calculated from the following current equation for the saturation region using the current transfer curve. That is, the current equation for the saturation region was converted into a graph relating $(I_{SD})^{1/2}$ and $V_G$, and the charge mobility was calculated from the slope of the converted graph:

$$I_{SD} = \frac{WC_0}{2L}\mu(V_G - V_T)^2$$

$$\sqrt{I_{SD}} = \sqrt{\frac{\mu C_0 W}{2L}}(V_g - V_T)$$

$$\text{slope} = \sqrt{\frac{\mu C_0 W}{2L}}$$

$$\mu_{FET} = (\text{slope})^2 \frac{2L}{C_0 W}$$

wherein $I_{SD}$ is source-drain current, $\mu$ or $\mu_{FET}$ is charge mobility, $C_o$ is oxide film capacitance, W is the channel width, L is the channel length, $V_G$ is the gate voltage, and $V_T$ is the threshold voltage.

The cut-off leakage current ($I_{off}$), which is the current flowing in the off-state, was determined to be the minimum current in the off-state in the on/off current ratio.

TABLE 1

| Organic Active Layer | Charge Mobility (cm²/Vs) | $I_{off}$(A) |
|---|---|---|
| Ex. 1 (Annealing at 100° C.) | $8 \times 10^{-3}$ | $10^{-11}$ |
| Ex. 2 (Annealing at 160° C.) | $6 \times 10^{-4}$ | $5 \times 10^{-11}$ |

As is apparent from Table 1, the OTFTs using the aromatic enediyne derivative of example embodiments may have decreased off-current of about $10^{-10}$ A or less while maintaining the performance thereof. Therefore, when applied to various electronic devices, e.g., TFTs, EL devices, solar cells and/or memory, the aromatic enediyne derivative was found to provide an organic semiconductor thin film having improved electrical properties.

As described hereinbefore, example embodiments may provide an aromatic enediyne derivative, an organic semiconductor thin film using the same, and an electronic device using the organic semiconductor thin film. The aromatic enediyne derivative of example embodiments, which is a low-molecular-weight organic semiconductor material having a structure, may be applied using a wet process at about room temperature and may be applicable to the processing of semiconductors having relatively large area. A chemically and electrically stable and reliable semiconductor thin film that has a regular molecular arrangement and does not crack may be provided. The organic semiconductor thin film of example embodiments may be effectively used in various fields, including OTFTs, EL devices, solar cells, and memory.

Although example embodiments have been disclosed for illustrative purposes, those skilled in the art will appreciate that various modifications, additions and substitutions are possible, without departing from the scope and spirit of example embodiments as disclosed in the accompanying claims.

What is claimed is:
1. An aromatic enediyne derivative, which is represented by Formula 3 below:

Formula 3 wherein, $R_1$, $R_2$, $R_3$, and $R_4$ are each independently selected from the group consisting of hydrogen, halogen, a nitro group, an amino group, a cyano group, —$SiR^1R^2R^3$ (in which $R^1$, $R^2$, and $R^3$ are each independently hydrogen or a $C_1$-$C_{10}$ alkyl group), a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted $C_6$-$C_{20}$ arylalkyl group, a substituted or unsubstituted $C_5$-$C_{30}$ aryloxy group, a substituted or unsubstituted $C_2$-$C_{30}$ heteroaryloxy group, a substituted or unsubstituted $C_1$-$C_{20}$ heteroalkyl group, and a substituted or unsubstituted $C_2$-$C_{30}$ heteroarylalkyl group, provided that none of $R_1$, $R_2$, $R_3$, and $R_4$ are hydrogen and at least one of $R_1$, $R_2$, $R_3$ and $R_4$ are different, and Ar is selected from the group consisting of a substituted or unsubstituted $C_2$-$C_{30}$ fused arylene group and a substituted or unsubstituted $C_2$-$C_{30}$ fused heteroarylene group, and is condensed with acetylene-substituted rings on both sides thereof.

2. The enediyne derivative as set forth in claim 1, wherein the Ar is selected from a group consisting of Formula 4 below, and is condensed with acetylene-substituted rings on both sides thereof:

Formula 4 wherein Y is carbon or a heteroatom, including nitrogen, oxygen, sulfur or selenium (Se), and
n is about 0 or a positive integer from about 1 to about 4.
3. An organic semiconductor thin film comprising the aromatic enediyne derivative of claim 1.

4. An electronic device, comprising the organic semiconductor thin film of claim 3 as a carrier transport layer.

5. The electronic device as set forth in claim 4, wherein the electronic device is a thin film transistor, an electroluminescent device, a solar cell, or memory.

6. A method of manufacturing an organic semiconductor thin film, comprising:
i) applying a precursor solution, including an aromatic enediyne derivative represented by Formula 3 below:

Formula 3 wherein, $R^1$, $R^2$, $R^3$, and $R^4$ are each independently selected from the group consisting of hydrogen, halogen, a nitro group, an amino group, a cyano group, —$SiR^1R^2R^3$ (in which $R^1$, $R^2$, and $R^3$ are each independently hydrogen or a $C_1$-$C_{10}$ alkyl group), a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ alkoxy group, a substituted or unsubstituted $C_6$-$C_{20}$ arylalkyl group, a substituted or unsubstituted $C_6$-$C_{30}$ aryloxy group, a substituted or unsubstituted $C_2$-$C_{30}$ heteroaryloxy group, a substituted or unsubstituted $C_1$-$C_{20}$ heteroalkyl group, and a substituted or unsubstituted $C_2$-$C_{30}$ heteroarylalkyl group, provided that none of $R_1$, $R_2$, $R_3$, and $R_4$ are hydrogen and at least one of $R_1$, $R_2$, $R_3$ and $R_4$ are different,
and
Ar is selected from the group consisting of a substituted or unsubstituted $C_2$-$C_{30}$ fused arylene group and a substituted or unsubstituted $C_2$-$C_{30}$ fused heteroarylene group, and is condensed with acetylene-substituted rings on both sides thereof, and an organic solvent, on a substrate to thus form a coating film; and
ii) heating the coating film to achieve crosslinking thereof, thereby forming a thin film.

7. The method as set forth in claim 6, wherein the precursor solution is prepared by mixing two or more aromatic enediyne derivatives represented by Formula 3.

8. The method as set forth in claim 6, wherein the aromatic enediyne derivative is included in the precursor solution in an amount of about 0.001 wt %~about 30 wt %.

9. The method as set forth in claim 6, wherein the organic solvent is at least one selected from the group consisting of an aliphatic hydrocarbon solvent, including hexane or heptane, an aromatic hydrocarbon solvent, including toluene, pyridine, quinoline, anisol, mesitylene, xylene or chlorobenzene, a ketone-based solvent, including methyl isobutyl ketone, 1-methyl-2-pyrrolidinone, cyclohexanone or acetone, an ether-based solvent, including tetrahydrofuran or isopropyl ether, an acetate-based solvent, including ethyl acetate, butyl acetate or propyleneglycol methyl ether acetate, an alcohol-based solvent, including isopropyl alcohol or butyl alcohol, an amide-based solvent, including dimethylacetamide or dimethylformamide, a halogen-based solvent, including dichloromethane or trichloromethane, a silicon-based solvent, and mixtures thereof.

10. The method as set forth in claim 6, wherein applying the precursor solution is performed using spin coating, dip coating, roll coating, screen coating, spray coating, spin casting, flow coating, screen printing, ink jetting, or drop casting.

11. The method as set forth in claim 6, wherein heating the coating film is performed at about 100° C.~about 250° C.

12. A method of manufacturing an electronic device comprising:
manufacturing the organic semiconductor thin film according to claim 6.

13. The method as set forth in claim 12, wherein the organic semiconductor thin film is a carrier transport layer.

14. The method as set forth in claim 12, wherein the electronic device is a thin film transistor, an electroluminescent device, a solar cell, or memory.

* * * * *

UNITED STATES PATENT AND TRADEMARK OFFICE
CERTIFICATE OF CORRECTION

| | |
|---|---|
| PATENT NO. | : 8,362,471 B2 |
| APPLICATION NO. | : 12/929078 |
| DATED | : January 29, 2013 |
| INVENTOR(S) | : Jeong Ii Park |

Page 1 of 1

It is certified that error appears in the above-identified patent and that said Letters Patent is hereby corrected as shown below:

On the Title Page, Item [75] Inventors should read:

[75] Inventors: Jeong Ii Park, Yongin-si (KR)

Signed and Sealed this
Eighteenth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,362,471 B2  
APPLICATION NO. : 12/929078  
DATED : January 29, 2013  
INVENTOR(S) : Jeong Il Park Page 1 of 1

It is certified that error appears in the above-identified patent and that said Letters Patent is hereby corrected as shown below:

On the Title Page, Item [75] Inventors, third inventor should read:

[75] Inventors: Jeong Il Park, Yongin-si (KR)

This certificate supersedes the Certificate of Correction issued June 18, 2013.

Signed and Sealed this  
Twenty-third Day of July, 2013

Teresa Stanek Rea  
*Acting Director of the United States Patent and Trademark Office*